United States Patent
Koch et al.

(10) Patent No.: US 7,694,675 B2
(45) Date of Patent: Apr. 13, 2010

(54) RESPIRATOR HUMIDIFIER

(75) Inventors: Jochim Koch, Ratzeburg (DE); Klaus Radomski, Lübeck (DE)

(73) Assignee: Dräger Medical AG & Co. KG, Lübeck (DE)

( * ) Notice: Subject to any disclaimer, the term of this patent is extended or adjusted under 35 U.S.C. 154(b) by 942 days.

(21) Appl. No.: 11/269,185

(22) Filed: Nov. 8, 2005

(65) Prior Publication Data

US 2006/0144395 A1 Jul. 6, 2006

(30) Foreign Application Priority Data

Jan. 4, 2005 (DE) .................. 10 2005 000 690

(51) Int. Cl.
- *A61M 15/00* (2006.01)
- *A61M 16/00* (2006.01)
- *H05B 3/00* (2006.01)

(52) U.S. Cl. .................. 128/203.17; 128/203.16; 128/204.17; 128/203.26; 392/394; 392/395; 392/386

(58) Field of Classification Search ............ 128/201.13, 128/203.17, 203.26, 204.17, 203.16; 392/394, 392/395
See application file for complete search history.

(56) References Cited

U.S. PATENT DOCUMENTS

| | | | | |
|---|---|---|---|---|
| 2,868,638 | A * | 1/1959 | Mott | 420/49 |
| 4,038,980 | A * | 8/1977 | Fodor | 128/203.27 |
| 5,062,145 | A * | 10/1991 | Zwaan et al. | 392/396 |
| 6,102,037 | A * | 8/2000 | Koch | 128/203.26 |
| 6,241,008 | B1 * | 6/2001 | Dunbar | 165/104.26 |
| 6,367,472 | B1 * | 4/2002 | Koch | 128/203.12 |
| 6,422,237 | B1 * | 7/2002 | Engel et al. | 128/204.21 |
| 6,540,916 | B2 * | 4/2003 | Patil | 210/502.1 |
| 7,144,473 | B2 * | 12/2006 | Baecke | 159/47.1 |
| 7,146,979 | B2 * | 12/2006 | Seakins et al. | 128/203.17 |
| 2003/0192953 | A1 | 10/2003 | Nitta | |
| 2004/0062531 | A1 * | 4/2004 | Triplett et al. | 392/395 |
| 2004/0079370 | A1 * | 4/2004 | Gradon et al. | 128/203.26 |

FOREIGN PATENT DOCUMENTS

| | | |
|---|---|---|
| DE | 198 08 590 | 9/1999 |
| GB | 1 182 421 A1 | 2/1970 |

\* cited by examiner

*Primary Examiner*—Patricia M Bianco
*Assistant Examiner*—Colin Stuart
(74) *Attorney, Agent, or Firm*—McGlew and Tuttle, P.C.

(57) ABSTRACT

An improved, pumpless respirator (ventilator) humidifier is provided with a water refilling device (1, 2) and with an electrically heated evaporator (5). The evaporator (5) has a tubular housing, which is filled with a porous sintered material. A front side of the housing is in liquid connection with the automatic water refilling device (1, 2) and the other front side is in connection with an evaporator chamber (4), through which breathing gas flows. The evaporator (5) is provided with a porous sintered glass or ceramic with a pore size of 10 μm to 40 μm in a first, lower, unheated area (14), and the evaporator (5) is provided with a porous sintered metal with a mean pore size of 50 μm to 200 μm in a second, upper area (15) heated by means of a heater (6).

20 Claims, 1 Drawing Sheet

RESPIRATOR HUMIDIFIER

CROSS REFERENCE TO RELATED APPLICATIONS

This application claims the benefit of priority under 35 U.S.C. § 119 of German Patent Application DE 10 2005 000 690.6 filed Jan. 4, 2005, the entire contents of which are incorporated herein by reference.

FIELD OF THE INVENTION

The present invention pertains to a respirator humidifier with an automatic water refilling means and with an electrically heated evaporator.

BACKGROUND OF THE INVENTION

The respirator humidifiers used hitherto have, in general, active humidifying systems, with heated evaporating chambers, via which the breathing gas to be humidified is sent. These humidifiers have a high airway resistance (resistance) and high compliance, which has a disturbing effect on the quality of the artificial respiration. In addition, these humidifying systems have a relatively long heat-up time, because the humidifier must first heat up the total amount of water present in the evaporator chamber before the humidifier can exert the desired humidifying output. This may take up to 30 minutes, and the humidifying output is reduced relatively greatly each time cold water is refilled, which is disadvantageous for the respiration therapy.

A humidifier of this type has become known from DE 198 08 590 C2 (corresponding to U.S. Pat. No. 6,102,037), where the dispensing of the amount of water, which depends on the tidal volume flow, with superheated steam is described. The drawback of this device is the necessary pump to dispense the amount of water. Thus, parts subject to wear are present, which must be replaced by the user at regular intervals.

SUMMARY OF THE INVENTION

The object of the present invention is accordingly to improve the prior-art respirator humidifier, so that its design is further simplified and, in particular, no pump is needed for the operation any longer.

According to the invention, a respirator humidifier is provided with an automatic water refilling means and with an electrically heated evaporator. The evaporator has a tubular housing, with a jacket which is filled with a porous material. One front side of the housing is in liquid connection with the water refilling means and the other front side is in connection with an evaporator chamber, through which breathing gas flows. The evaporator is provided with a porous sintered glass or ceramic with a pore size of 10 μm to 40 μm in a first, lower, unheated area. The evaporator is provided with a porous sintered metal with a mean pore size of 50 μm to 200 μm in a second, upper area heated by means of a heater arranged on the jacket side of the housing.

An essential advantage of the respirator humidifier according to the present invention is that the moisture is dispensed directly on the basis of the heating output at the housing of the evaporator and that no pump is necessary, so that no parts subject to wear need to be replaced by the user, either.

The sintered metal may consist of a stainless steel. A stainless steel that is a chromium-nickel steel is advantageous.

The evaporator may be provided with a first temperature sensor in the second, upper area for controlling the heating output of the heater. The evaporator may also be provided with an additional, second temperature sensor in the first, lower area for controlling the heating output of the heater, so that overheating of the first area is prevented from occurring. A breathing gas volume flow sensor and a third temperature sensor may be provided in front of the evaporator chamber and a fourth temperature sensor may be provided behind the evaporator chamber for controlling the heating output of the heater as a function of the measured heating of the measured breathing gas volume flow.

The heating output of the heater may be controlled first as a function of the measured heating of the measured breathing gas volume flow, providing that when a preset, upper limit value of the temperature measured by means of the second temperature sensor in the first, lower area is exceeded, the heating output of the heater is reduced or interrupted.

The length to volume ratio of the sintered glass or ceramic arranged in the first, lower area to the porous sintered metal arranged in the second, upper area may advantageously be approximately from 1:4 to 1:6.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
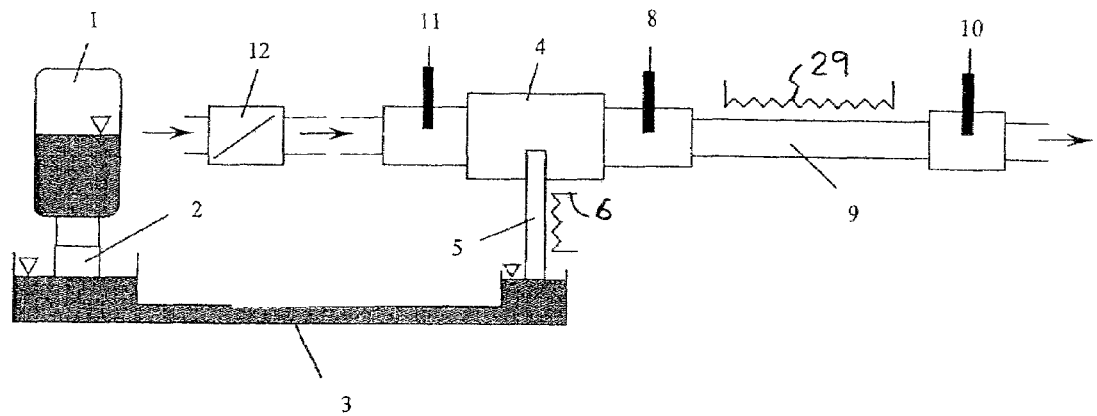
FIG. 1 is a schematic view showing the arrangement of a respirator humidifier for humidifying a breathing gas flow.
Figure 2:
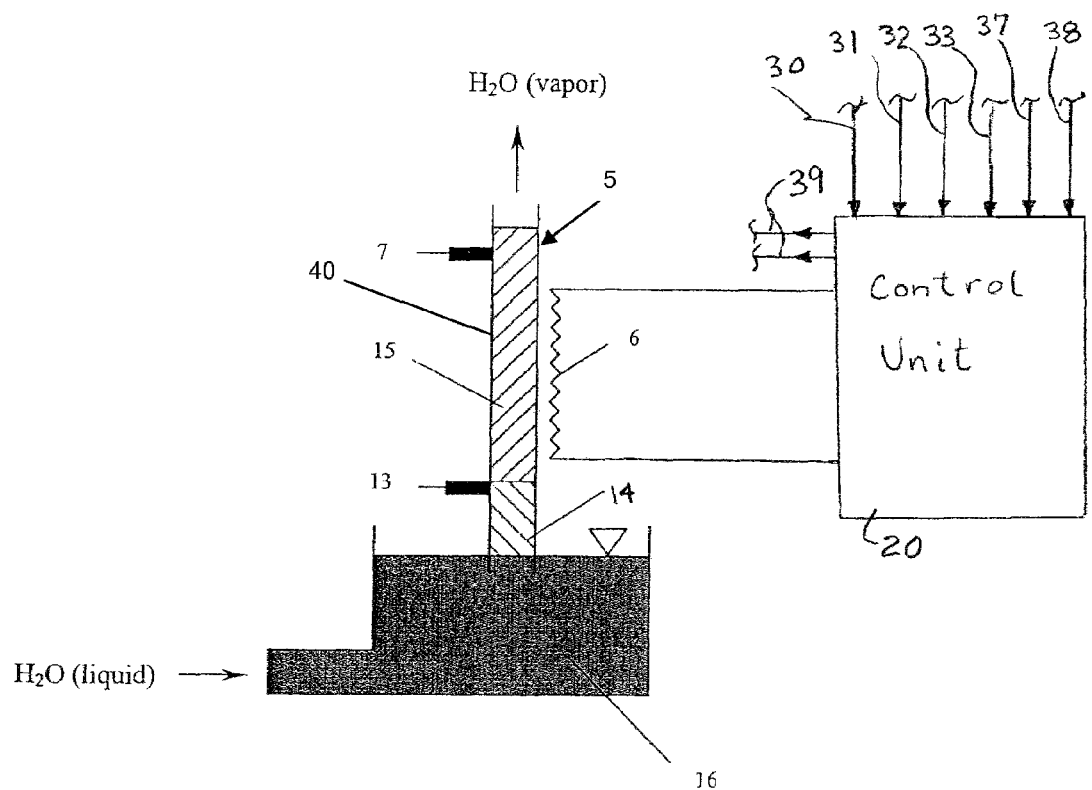
FIG. 2 is a schematic view showing a detailed design of a respirator humidifier.

Referring to the drawings in particular, according to FIG. 1, sterile water is made available for the evaporator 5 having especially a heated tubular, metallic housing from an automatic water refilling means 1, 2, containing a water tank 1 and a level regulator 2 via a connection line 3. The metallic housing of the evaporator 5 defines a jacket 40. The outlet side of the evaporator 5 is connected directly to an evaporator chamber 4, through which breathing gas flows in the direction of the arrow to a patient who is, e.g., respirated artificially. The evaporator 5 is heated directly at the tubular housing by means of the electric heater 6. A first temperature sensor 7, designed preferably as a thermostat, controls the temperature in the second, upper area 15, which temperature is above the boiling point of water, especially in a temperature range of about 140° C. to 400° C. during operation. The evaporator 5 is provided with an additional, second temperature sensor 13 in the first, lower area 14 for controlling the heating output of the said heater 6, so that overheating of the first area 14 is prevented from occurring. The breathing gas to the patient is heated to the desired breathing gas temperature by the addition of steam and the moisture content is increased in the breathing gas. A third temperature sensor 11 is provided. The resulting mixture temperature of the humidified breathing gas is measured and controlled by means of the fourth temperature sensor 8. The breathing gas is delivered to the patient via a heated flexible tube 9 (heated by heater 29). The breathing gas temperature is optionally maintained at a constant value by means of the flexible tube heater 29 and by means of another temperature sensor 10. The tubular evaporator housing preferably consists of a steel alloy and is heated from the outside directly by means of the electric heater 6. A porous sintered glass or ceramic with poor thermal conductivity is inserted on the liquid/water side 16 (FIG. 2) and it forms the first, lower, unheated area 14 of the evaporator 5, so that high temperatures will not develop in this area 14. The pore size of a suitable sintered glass or ceramic is in the range of 10 μm to 40 μm. The function of the unheated sintered glass or ceramic with low porosity and high capillary action is a wick action and it shall prevent the liquid from being sent back due to the respiration pressure. In addition, the liquid is prevented from being heated in this region by the "poor" thermal conductivity (the heat-insulating action) of the sintered glass or ceramic.

Sintered glass or ceramic is manufactured with low porosity, so that the water cannot be forced back by the respiration pressure present over the evaporator chamber 4, i.e., as was revealed by both calculations and confirmed by measurements, the capillary pressure within the sintered glass or ceramic exceeds the highest possible hypothetical respiration pressure of, for example, 100 mbar at a pore size of less than 30 μm. To compensate a lower respiration pressure of, e.g., 50 mbar, it would be possible to use a sintered glass or ceramic with a larger pore size of, e.g., about 40 μm in order to compensate the respiration pressure in the evaporator 5.

In the second, upper area 15, the evaporator tube is filled with a sintered metal with good heat conductivity, because the highest evaporating output is transferred in this area. The area 15 is completely surrounded by the electric heater 6. The sintered metal preferably consists of a porous, stainless steel, for example, a chromium-nickel alloy, and has a mean pore size of 50 μm to 200 μm. It is guaranteed by the sintered metal with good heat conductivity that the core of the sintered material also offers the same high evaporating temperatures, so that the interpenetration of cold water or colder steam is prevented from occurring. The evaporator tube is connected on its cold side with the liquid 16 to be evaporated, which is drawn by the capillary action of the sintered glass or ceramic into the evaporator tube.

The humidifying function can be checked by comparing the temperature increase between the inlet temperature and outlet temperature measured by means of the third and fourth temperature sensors 11, 8. For this, a control unit 20 may be provided. In the example, the control unit 20 (which may include a microprocessor) is connected to each of the sensors, namely to sensor 10 by line 30, to sensor 11 by line 31, to breathing gas volume sensor 12 by line 32, to sensor 13 by line 33, to sensor 7 by line 37, and to sensor 8 by line 38. The control unit 20 (with suitable actuators/drivers) is connected to the electric heater 6 as well as the electric heater 9. The desired humidification can be controlled based on a thermodynamic mixture equation between the enthalpies of the amounts of breathing gas and steam fed in, on the one hand, and the resulting amount of humidified breathing gas, on the other hand. However, the breathing gas volume flow currently being delivered, which is detected by means of the breathing gas volume sensor 12 or is made available, as an alternative, by the connected respirator, which is not shown and is arranged farther to the left in FIG. 1, is necessary for this. The present arrangement is described only as an example. Other variants of this are also conceivable, especially with the use of other materials, which possess the desired physical properties, especially novel materials with the desired porosities and heat conduction properties, for example, those based on plastics, mixtures or alloys. If the breathing gas leaving the evaporator chamber 4 is not heated, no evaporation of water has taken place. If the breathing gas is heated above the desired breathing gas temperature set point, too much steam was fed in, so that the actuation of the water dispensing means and consequently of the heater 6 can be correspondingly corrected. Overdosage of the humidifier is reliably ruled out due to the arrangement being described. To generate, for example, 2.5 mg of steam per minute and at a breathing gas volume flow of about 25 L per minute at the outlet of the evaporator chamber 4 and at an internal diameter of 8 mm of the tubular housing of the evaporator 5, the height of the first, lower area 14 provided with sintered glass or ceramic is about 10 mm, and the height of the second, upper area 15 provided with porous sintered metal is about 50 mm, i.e., the length to volume ratio is 1:5.

The control of the heating output of the heater 6 can be provided with the first temperature sensor 7 in the second, upper area 15. Further with the evaporator 5 provided with an additional, second temperature sensor 13 in the said first, lower area the control of the heating output of the heater 6 may also be based on the temperature sensed by second temperature sensor 13 so that overheating of the first area is prevented from occurring. The breathing gas volume flow sensor and the third temperature sensor 11 provided in front (upstream) of the evaporator chamber 4 and the fourth temperature sensor 8 is provided behind (downstream) of the evaporator chamber 4 may be used for controlling the heating output of the said heater 6 as a function of the measured heating of the measured breathing gas volume flow. The heating output of the heater 6 may be controlled first as a function of the measured heating of the measured breathing gas volume flow, providing that when a preset, upper limit value of the temperature measured by means of the second temperature sensor 13 in the said first, lower area 14 is exceeded, the heating output of the heater 6 is reduced or interrupted.

While a specific embodiment of the invention has been shown and described in detail to illustrate the application of the principles of the invention, it will be understood that the invention may be embodied otherwise without departing from such principles.

What is claimed is:

1. A respirator humidifier, comprising:
    an evaporator chamber;
    an automatic water refilling device;
    an evaporator with a tubular housing with a jacket having an outer jacket side and an inside filled with a porous material, wherein one end of the housing is in liquid connection with the water refilling device and another end of said housing is in connection with said evaporator chamber, through which breathing gas flows; and
    a heater arranged externally of said jacket of said housing for heating said housing, said porous material including a porous sintered glass or ceramic with a pore size of 10 μm to 40 μm in a first, lower, unheated area of said jacket and a porous sintered metal with a mean pore size of 50 μm to 200 μm in a second, upper area heated by said heater, said porous material defining a capillary action delivery means for delivering water from said automatic refilling device to said evaporator chamber via capillary action.

2. A respirator humidifier in accordance with claim 1, wherein the sintered metal consists of a stainless steel.

3. A respirator humidifier in accordance with claim 1, wherein said evaporator is provided with a first temperature sensor in said second, upper area, for controlling a heating output of the heater.

4. A respirator humidifier in accordance with claim 3, wherein said evaporator is provided with an additional, second temperature sensor in said first, lower area for controlling the heating output of the heater, so that overheating of the first area is prevented from occurring.

5. A respirator humidifier in accordance with claim 4, further comprising a breathing gas volume flow sensor provided upstream of said evaporator chamber with respect to a direction of flow and a third temperature sensor provided upstream of said evaporator chamber with respect to the direction of flow and a fourth temperature sensor provided downstream of said evaporator chamber with respect to the direction of flow for controlling the heating output of the heater as a function of the measured heating of the measured breathing gas volume flow.

6. A respirator humidifier in accordance with claim 5, wherein the heating output of the heater is controlled first as a function of the measured heating of the measured breathing gas volume flow, providing that when a preset, upper limit value of the temperature measured by means of said second temperature sensor in the first, lower area is exceeded, the heating output of the heater is reduced or interrupted.

7. A respirator humidifier in accordance with claim 1, wherein the length to volume ratio of the sintered glass or ceramic arranged in the first, lower area to the porous sintered metal arranged in the second, upper area is approximately 1:4 to 1:6.

8. A respirator humidifier in accordance with claim 1, wherein the sintered metal comprises a chromium-nickel steel.

9. A respirator humidifier in accordance with claim 1, further comprising a breathing gas volume flow sensor provided upstream of said evaporator chamber with respect to a direction of flow and a leading temperature sensor provided upstream of said evaporator chamber with respect to the direction of flow and a trailing temperature sensor provided downstream of said evaporator chamber with respect to the direction of flow for controlling the heating output of the heater as a function of the measured heating of the measured breathing gas volume flow.

10. A respirator humidifier in accordance with claim 3, further comprising a breathing gas volume flow sensor provided upstream of said evaporator chamber wherein the heating output of the heater is controlled first as a function of the measured heating of the measured breathing gas volume flow, providing that when a preset, upper limit value of the temperature measured by means of said second temperature sensor in the first, lower area is exceeded, the heating output of the heater is reduced or interrupted.

11. A respirator humidifier, comprising:
an evaporator chamber;
a water reservoir;
an automatic water refilling means for maintaining said water reservoir at a fill level;
an evaporator with a tubular housing having an outer surface, said tubular housing having a first housing inner portion and a second housing inner portion, said first housing inner portion being composed of a first porous material, said second housing inner portion being composed of a second porous material; and
a heater external to said tubular housing of said evaporator for heating said second housing inner portion, said first porous material including a porous sintered material of a first thermal conductivity with a pore size of 10 µm to 40 µm, said first housing inner portion not being heated via said heater, said second porous material having a second thermal conductivity with a mean pore size of 50 µm to 200 µm, said second porous material being heated via said heater when said heater is activated, said first porous material and said second porous material defining a capillary delivery means for delivering the water from said water reservoir to said evaporator chamber via capillary action, said second thermal conductivity being greater than said first thermal conductivity.

12. A respirator humidifier in accordance with claim 11, wherein said first porous material includes a porous sintered glass or ceramic and, said second porous material includes a porous sintered metal.

13. A respirator humidifier in accordance with claim 11, wherein said evaporator is provided with a first temperature sensor in said second housing inner portion for controlling a heating output of the heater.

14. A respirator humidifier in accordance with claim 13, wherein said evaporator is provided with an additional, second temperature sensor in said first housing inner portion for controlling the heating output of the heater, so that overheating of said first housing inner is reduced.

15. A respirator humidifier in accordance with claim 14, further comprising a breathing gas volume flow sensor provided upstream of said evaporator chamber with respect to a direction of flow and a third temperature sensor provided upstream of said evaporator chamber with respect to the direction of flow and a fourth temperature sensor provided downstream of said evaporator chamber with respect to the direction of flow for controlling the heating output of the heater as a function of the measured heating of the measured breathing gas volume flow.

16. A respirator humidifier in accordance with claim 15, wherein the heating output of the heater is controlled first as a function of the measured heating of the measured breathing gas volume flow, providing that when a preset, upper limit value of the temperature measured by means of said second temperature sensor in the first housing inner portion is exceeded, the heating output of the heater is reduced or interrupted.

17. A respirator humidifier in accordance with claim 11, wherein the length to volume ratio of the sintered glass or ceramic arranged in the first housing inner portion to the porous sintered metal arranged in the second housing inner portion is approximately 1:4 to 1:6.

18. A respirator humidifier in accordance with claim 12, wherein the sintered metal comprises one or more of a chromium-nickel steel and a stainless steel.

19. A respirator humidifier in accordance with claim 11, further comprising a breathing gas volume flow sensor provided upstream of said evaporator chamber with respect to a direction of flow and a leading temperature sensor provided upstream of said evaporator chamber with respect to the direction of flow and a trailing temperature sensor provided downstream of said evaporator chamber with respect to the direction of flow for controlling the heating output of the heater as a function of the measured heating of the measured breathing gas volume flow.

20. A respirator humidifier, comprising:
an evaporator chamber;
a water reservoir;
an automatic water refilling means for delivering water to said water reservoir such that said water reservoir is maintained at a fill level;
an evaporator with a tubular housing having an outer surface, said tubular housing having a first housing inner portion and a second housing inner portion, said first housing inner portion being composed of a first porous material having a first thermal conductivity, said second housing inner portion being composed of a second porous material having a second thermal conductivity, one end of said housing being in contact with said water reservoir and another end of said housing being connected to said evaporator chamber, said first thermal conductivity being less than said second thermal conductivity; and a heater for heating said evaporator from the outside, said first porous material including a porous sintered glass or ceramic with a pore size of 10 μm to 40 μm, said first housing inner portion not being heated via said heater, said second porous material including a porous sintered metal with a mean pore size of 50 μm to 200 μm, said second porous material being heated via said heater when said heater is activated, said first porous material and said second porous material defining a means for producing a capillary action such that water passes from said water reservoir to said evaporator via said capillary action, wherein said heater evaporates the water in said second housing inner portion when said heater is activated.

* * * * *